US00PP36090P2

(12) United States Plant Patent
Weisel

(10) Patent No.: US PP36,090 P2
(45) Date of Patent: Sep. 3, 2024

(54) ***DIPLADENIA* PLANT NAMED 'TSF 004'**

(50) Latin Name: *Dipladenia sanderi*
Varietal Denomination: TSF 004

(71) Applicant: TreeSap Farms LLC, Houston, TX (US)

(72) Inventor: Lawrence Harold Weisel, Carlsbad, CA (US)

(73) Assignee: Treesap Farms LLC, Houston, TX (US)

( * ) Notice: Subject to any disclaimer, the term of this patent is extended or adjusted under 35 U.S.C. 154(b) by 0 days.

(21) Appl. No.: 18/134,422

(22) Filed: Apr. 13, 2023

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
CPC ..... A01H 5/02; A01H 5/00; A01H 6/088
See application file for complete search history.

(56) References Cited

U.S. PATENT DOCUMENTS

PP9,118 P * 4/1995 Petersen ..... Plt./232
PP15,359 P2 * 11/2004 Proud ..... A01H 6/088 Plt./232
PP23,293 P2 * 1/2013 Fisher ..... A01H 5/02 Plt./232

OTHER PUBLICATIONS

Syngenta Flowers retrieved from the Internet at https://www.syngentaflowers-us.com/products/search/flower/botanical_name/mandevilla-hybrida-2701/category/annual-116/category/annual-combination-10726/type/vegetative-326?keywords=madinia&items_per_page=12, 5 pp. (Year: 2024).*

* cited by examiner

*Primary Examiner* — June Hwu
(74) *Attorney, Agent, or Firm* — Cassandra Bright

(57) ABSTRACT

A new and distinct *Dipladenia* cultivar named 'TSF 004' is disclosed, characterized by orange-red to red flowers and variegated foliage which has been proven stable. The new variety is a *Dipladenia*, typically produced as an indoor ornamental plant.

1 Drawing Sheet

Latin name of the genus and species: *Dipladenia sanderi.* Variety denomination: 'TSF 004'.

BACKGROUND OF THE INVENTION

The new cultivar is a product of chance discovery. The new variety was discovered as a naturally occurring whole plant mutation of the *Dipladenia sanderi* 'Cerise' U.S. Plant Pat. No. 9,118. The selection was made among a group of the parent plants growing in a hoophouse at a commercial nursery Mar. 1, 2020 in Escondido, California.

Asexual reproduction of the new cultivar 'TSF 004' was first performed at a commercial nursery in Escondido, California by terminal vegetative cuttings in April of 2020. Subsequent propagation has shown that the unique features of this cultivar are stable and reproduced true to type.

The following traits have been repeatedly observed and are determined to be the unique characteristics of 'TSF 004.' These characteristics in combination distinguish 'TSF 004' as a new and distinct *Dipladenia* cultivar:

1. Orange-red to red colored flowers.
2. Cream colored variegated margins of foliage.
3. Stability of variegation in successive vegetative propagation.

PARENT COMPARISON

Plants of the new cultivar 'TSF 004' are similar to the seed parent in most horticultural characteristics. The new variety, however, differs in the following:

1. The new variety has variegated foliage; the parent variety has solid colored foliage.

COMMERCIAL COMPARISON

'TSF 004' can be compared to compared to the commercial variety *Dipladenia Mandevilla* 'Monproud', U.S. Plant Pat. No. 15,359. Plants of 'Monproud' are similar to plants of 'TSF 004' in most horticultural characteristics, however, plants of 'TSF 004' differ in the following:

1. Flower color of 'TSF 004' is orange-red and red; flower color of this comparator is red-purple with some white streaks.
2. Average flower size of the new variety is 6.5 cm in diameter and 7.5 cm in length; average flower size of this comparator is 5.5 cm in diameter and 6 cm in length.

'TSF 004' can aldo be compared to compared to the commercial variety *Mandevilla* 'FGDIPIRV', U.S. Plant Pat. No. 23,293. Plants of 'FGDIPIRV' are similar to plants of 'TSF 004' in most horticultural characteristics, however, plants of 'TSF 004' differ in the following:

1. Average flower length of the new variety is 7.5 cm; average flower length of this comparator is 5 to 6 cm.
2. Mature flower color of the new variety is Orange-Red N34A flushed Red 53A with no distinct venation coloration in petals; mature flower color of this comparator is varying shades of Red 53A, 53B, 46A and 46B with dull orange-red venation.

3. Height of the new variety at 10 months is 35 cm; height of this comparator at 8 months is 96 cm.

BRIEF DESCRIPTION OF THE PHOTOGRAPH

The accompanying drawing illustrates in full color typical plants of 'TSF 004' grown outdoors in Escondido, CA. This plants are approximately 12 months old, shown in an 1-gallon pots. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'TSF 004' plants grown outdoors in Escondido, CA. Temperatures ranged from 10° C. to 18° C. at night to 15° C. to 30° C. during the day. No artificial light, photoperiodic treatments were given to the plants. Measurements and numerical values represent averages of typical plant types.

Botanical classification: *Dipladenia sanderi* TSF 004'.

PROPAGATION

Time to initiate roots: About 15 days at approximately 30° C. in the summer. About 25 days at 18° C. in the winter.

Time to produce a rooted cutting: About 50 days at 20 to 30° C.

Root description: Freely branching and white-brown in color. Not accurately measured with RHS chart.

PLANT

Growth habit: Vining evergreen flowering plant. Initially upright, then vining, requiring support to maintain upright habit. Typically, plants are pinched approximately 3 months after planting a rooted cutting to encourage branching.

Age of plant described: 10 months.

Container size: 1 gallon.

Height: Approximately 35 cm.

Plant spread: Approximately 26 cm.

Growth rate: Moderate.

Branching characteristics: Strong branching occurs after pinch.

Length of primary lateral branches: Approximately 10 to 16 cm.

Diameter of lateral branches: Approximately 4 mm.

Internode length: Approximately 10 to 15 mm.

Stem texture: Glabrous.

Color main lateral branches: Near RHS Greyed-Orange 164A flushed Greyed-Green 198C.

Stem anthocyanin: Absent.

Climbing tendrils: None present on 10 month old plant.

FOLIAGE

Leaf:

*Arrangement.*—Opposite, simple.

*Average length.*—Approximately 5.5 cm to 7.0 cm.

*Average width.*—Approximately 2.5 cm to 3.5 cm.

*Shape of blade.*—Elliptic.

*Apex.*—Acute.

*Base.*—Obtuse.

*Attachment.*—Petiolate.

*Margin.*—Entire. Weakly undulate.

*Texture of top surface.*—Glabrous.

*Texture of bottom surface.*—Glabrous.

*Leaf internode length.*—Approximately 1 cm.

*Leaf bulging between veins.*—Absent.

*Color.*—Young foliage upper side: Variegated: marginal region mostly Yellow 4D. Blotched and marbled in center, Green 137A, 137B, and 137C. Very slightly flushed near Red 52A and 52C along margin. Young foliage under side: Variegated: marginal region mostly Yellow 4D. blotched and marbled in center Greyed-Green 191C and Green 137C. Mature foliage upper side: Variegated: marginal region mostly Yellow 4D. blotched and marbled in center Greyed-Green 191C, Green 137A, 137B, and 137C. Mature foliage under side: Variegated: marginal region mostly Yellow 4D. blotched and marbled in center Greyed-Green 191C, Green 137C, and 137D.

*Venation.*—Type: Pinnate Venation color upper side: Near RHS Yellow-Green 144C. Lightly flushed Red 52C near base. Venation color under side: Near RHS Yellow-Green 145C.

*Petiole.*—Average Length: Approximately 1.0 cm. Color: Upper surface near Red 51C; lower surface near Yellow-Green 145D. Diameter: Approximately 2 mm. Texture: Glabrous. Petiole anthocyanin intensity: Strong on upper surface, weak on lower surface.

FLOWER

Natural flowering season: Naturally flowers Summer through late Autumn.

Inflorescence type and habit: Single salverform flower; terminal or axillary; flowers face outward and upward.

Rate of flower opening: Approximately 3 days from bud to fully opened flower.

Flower Longevity on plant: 4 to 5 days, after fully opened. Self-cleaning.

Quantity of flowers: Young plants have a range of 3 to 10 flowers and buds at all times.

Inflorescence size:

*Diameter.*—Approximately 6.5 cm.

*Length.*—Approximately 7.5 cm.

*Corolla tube length.*—Approximately 4.5 cm.

*Throat diameter.*—Approximately 1.9 cm.

Corolla:

*Petal arrangement.*—Single whorl of 5, fused into flared trumpet. Strongly asymmetric.

*Size.*—Lobe Length: 3.5 cm. Lobe Width: 2.5 cm.

*Margin.*—Entire.

*Apex.*—Acute.

*Texture.*—Smooth, velvety.

Color: petals:

*When opening.*—Upper surface: Near RHS Orange-Red N34A flushed Red 53A. Lower surface: Near RHS Orange-Red N34A streaked Red 46A.

*Fully opened.*—Upper surface: Near RHS Orange-Red N34A flushed Red 53A. Lower surface: Near RHS Orange-Red N34A streaked Red 46A. Tube color (interior): Near RHS Yellow-Orange 17A with streaks near RHS Orange-Red N34A. Tube color (exterior): Near RHS White 155D with streaks near RHS Red 53A.

Bud:

*Shape.*—Ovate to Lanceolate.

*Length.*—Approximately 5.5 cm.

*Diameter.*—Approximately 1.2 cm.

*Color.*—Near RHS Red 53A streaked White 155D at base; near RHS White 155D in middle; near RHS Red 53A at apex.

Sepals:

*Arrangement.*—5 per flower in a single whorl; fused.

*Shape.*—Narrowly deltoid.

*Quantity.*—5.

*Length.*—Approximately 6 mm.

*Width.*—Approximately 2 mm.

*Margin.*—Entire.

*Apex.*—Acuminate.

*Texture.*—Smooth, waxy.

*Color.*—Upper surface: Near RHS Yellow-Green 145D flushed Red 53A. Lower surface: Near RHS Yellow-Green 145D flushed Red 53A.

Peduncles:

*Length.*—Approximately 2.5 cm.

*Width.*—Approximately 3 mm.

*Angle.*—Straight or slight undulation.

*Strength.*—Flexible and strong.

*Color.*—Near RHS Yellow-Green 145D. Moderate intensity anthocyanin, Red 53C.

Fragrance: None.

REPRODUCTIVE ORGANS

Stamens:

*Number.*—5, anthers fused together at tips, filaments fused to corolla.

*Anther length.*—1 cm.

*Anther color.*—Near RHS Yellow 4C.

*Anther shape.*—Oblong.

*Pollen.*—None observed.

Pistil:

*Number.*—1.

*Length.*—Approximately 2.5 cm.

*Style color.*—Near RHS White 155D.

*Stigma.*—Shape: Globular. Color: Near RHS Red 53D. Ovary color: Near RHS Yellow-Green 145D.

OTHER CHARACTERISTICS

Disease resistance: Neither resistance nor susceptibility to normal diseases and pests of *Dipladenia* have been observed.

Drought tolerance and cold tolerance: Tolerates temperatures from approximately 0° C.to 40° C. and does not tolerate drought.

Fruit/seed production: Not observed.

What is claimed is:

1. A new and distinct cultivar of *Dipladenia* plant named 'TSF 004' as herein illustrated and described.

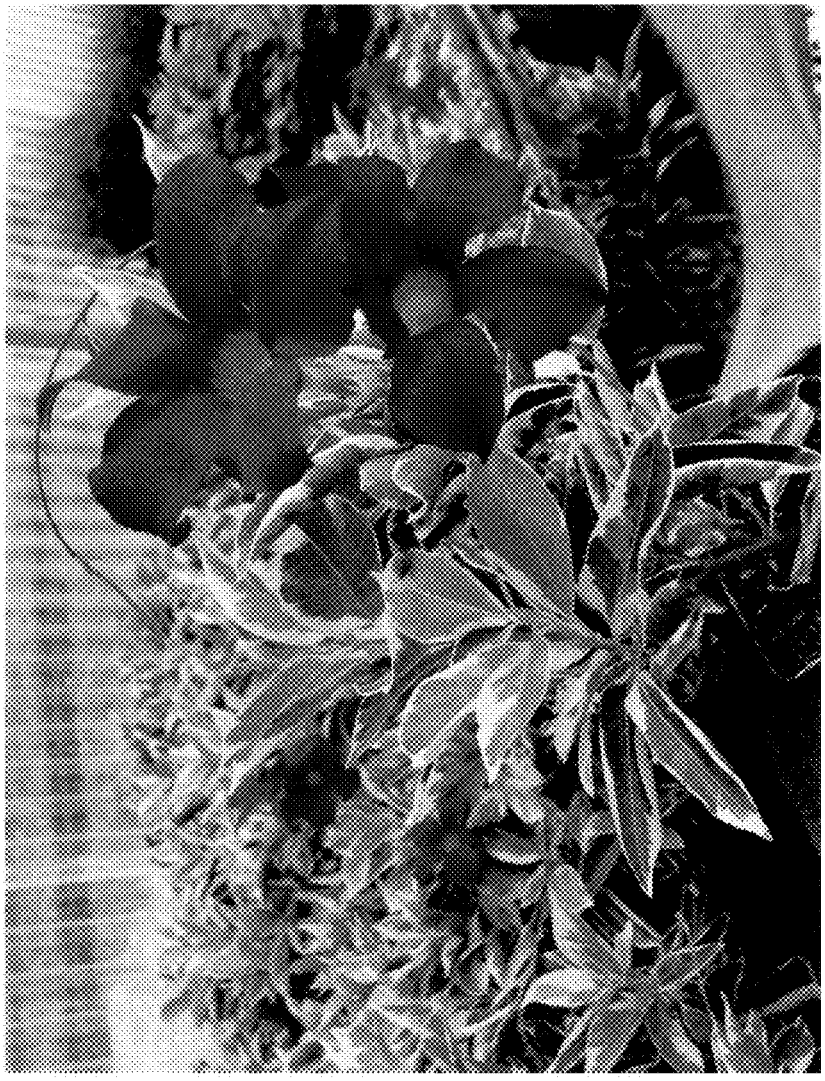

* * * * *